United States Patent [19]

White et al.

[11] 4,146,553

[45] Mar. 27, 1979

[54] INTERMEDIATES FOR SYNTHESIZING 11-DEOXYPROSTAGLANDINS

[75] Inventors: William L. White, Holliston; Francis Johnson, Setauket, both of N.Y.

[73] Assignee: The Dow Chemical Company, Midland, Mich.

[21] Appl. No.: 916,670

[22] Filed: Jun. 19, 1978

Related U.S. Application Data

[62] Division of Ser. No. 798,537, May 19, 1977, Pat. No. 4,125,556.

[51] Int. Cl.$^2$ .................... C07C 69/74; C07C 121/48
[52] U.S. Cl. ............................. 260/464; 260/465 D; 560/121; 560/122
[58] Field of Search .............................. 560/121, 122; 260/465 D, 464

[56] References Cited

U.S. PATENT DOCUMENTS

| 4,045,465 | 8/1977 | Hess et al. | 260/464 |
| 4,055,593 | 10/1977 | Weinshenker et al. | 260/464 X |

Primary Examiner—Dolph H. Torrence

[57] ABSTRACT

Improved procedures and intermediates for synthesizing 11-deoxyprostaglandins wherein trans-2,3-dicarbomethoxycyclopentanone is prepared by the novel kinetically-controlled cyclization of 1,2,4-tricarbomethoxybutane using a dispersion of sodium hydride in dry p-xylene. Selective alcoholysis of the 2-position carbomethoxy group with benzyl alcohol, followed by alkylation allows for a wide range of upper side chains to be introduced at the 2-position of the cyclopentanone ring. The unwanted carbobenzyloxy group at the 2-position can then be removed easily by controlled hydrogenolysis followed by decarboxylation. This procedure allows for simultaneous epimerization of the 2-position side chain to the desired trans-configuration, relative to the carbomethoxy group in the 3-position, as well as for reduction of the 2-hexynyl moiety of the side chain to the desired cis-olefinic group of the $E_2$-type 11-deoxyprostaglandins, or through total reduction to the alkane upper side chain of $E_1$-type prostaglandin analogs. Modification thereafter of the carbonyl group at the 3-position of the cyclopentanone ring by a variety of reagents allows introduction of the lower side chain present in the prostaglandins themselves or a variety of other side chains derived from the 3-carboxy-, 3-hydroxymethyl- or 3-aldehyde-substituted cyclopentanone ring. From the latter, 11-deoxyprostaglandins can be prepared by known procedures.

6 Claims, No Drawings

INTERMEDIATES FOR SYNTHESIZING 11-DEOXYPROSTAGLANDINS

CROSS REFERENCE TO RELATED APPLICATION

This is a division, of application Ser. No. 798,537, filed May 19, 1977, now U.S. Pat. No. 4,125,556.

SUMMARY OF THE INVENTION

This invention concerns improved methods and intermediates for synthesizing 11-deoxyprostaglandin intermediates. In the new synthetic route, trans-2,3-dicarbomethoxycyclopentanone is readily prepared by a novel process. A novel alcoholysis with benzyl alcohol thereafter substitutes a 2-carbobenzyloxy group. Any required upper side chain thereafter can easily be introduced in its entirety by an alkylation procedure. The unwanted carbobenzyloxy group at the 2-position of the resulting compound is readily removed by controlled hydrogenolysis followed by decarboxylation. This procedure allows for simultaneous epimerization of the 2-position side chain to the desired trans-configuration, relative to the carbomethoxy group in the 3-position, as well as for reduction of the 2-hexynyl moiety of the side chain to the desired cis-olefinic group of the $E_2$-type 11-deoxyprostaglandins, or through total reduction to the alkane upper side chain of $E_1$-type prostaglandin analogs. Thereafter, modification of the carbonyl group at the 3-position of the cyclopentanone ring, readily accomplished by a variety of reagents, allows introduction of the lower side chain present in the prostaglandins themselves or a variety of other side chains derived from the 3-carboxy-, the 3-hydroxymethyl- or the 3-aldehyde-substituted cyclopentanone ring. From the latter, 11-deoxyprostaglandins are readily synthesized by known procedures.

DESCRIPTION OF SOME PREFERRED EMBODIMENTS

The starting material used in the novel processes for making the intermediates for 11-deoxyprostaglandins is 1,2,4-tricarbomethoxybutane. This compound may be prepared by the procedure of U.S. Pat. No. 2,203,628 by nitric acid oxidation of a $\Delta^3$-cyclohexene which is substituted in at least one of the 1- and 2-positions of the cyclohexene nucleus by a carboxylic group. Thereafter, the resulting 1,2,4-tricarboxybutane is esterified to the trimethyl ester with methanol in the presence of an acidic catalyst, following well-known procedures. The series of reactions involved in the novel synthesis may be depicted by the following schematic representation:

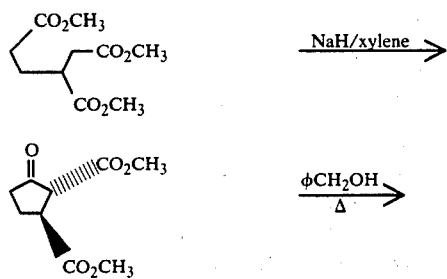
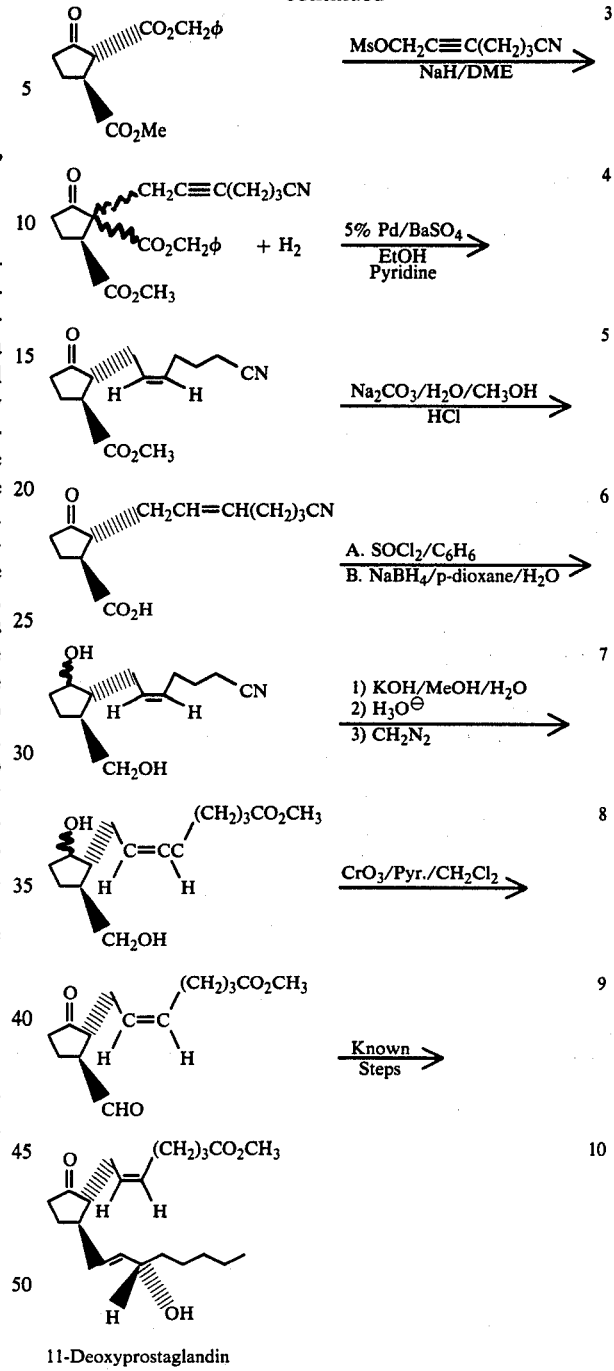

STEP 1

The first step in the synthetic scheme is the conversion of 1,2,4-tricarbomethoxybutane to trans-2,3-dicarbomethoxycyclopentanone. This is carried out by reacting the starting material with alkali metal hydride, used as a dispersion in mineral oil, the reaction medium being dry p-xylene in the presence of a trace of anhydrous methanol. The starting material is added stepwise to the reaction medium. The reaction temperature is maintained between about 20° C. and about 40° C. while the reaction mixture is stirred. Stirring is continued for a short time after addition of the starting material is complete, the resulting viscous mixture is diluted with water and the phases are separated. The aqueous phase is immediately acidified by addition thereto of citric acid monohydrate with stirring. The crude product is extracted several times, advantageously three times, with ethyl acetate and the combined organic phases are washed with water and twice with sodium chloride brine and dried over anhydrous magnesium sulfate. The solution is filtered, treated with decolorizing carbon, again filtered and concentrated in vacuo to give crude product which crystallizes upon seeding. This material, trans-2,3-dicarbomethoxycyclopentanone, 90–95% pure as determined by VPC, may be employed directly in the next step. Preferably, it should first be recrystallized from ethyl ether/petroleum ether.

Prior art procedures for making the product of the first step (J. Chem. Soc., 89, 1640, Helv. Chim. Acta. 17, 183 and Zh. Obsh. Khim. 34, 828) have always given a mixture of the first step product and its isomeric cyclization product 2,4-dicarbomethoxycyclopentanone. By the novel procedure just described, virtually none of the unwanted 2,4-isomer (<10%) is produced.

STEP 2

In this step, alcoholysis with benzyl alcohol provides a carbobenzyloxy group in place of the carbomethoxy group at the 2-position prior to the introduction at the 2-position of a required side chain. This is accomplished by stirring a mixture of substantially equimolar proportions of 2,3-dicarbomethoxycyclopentanone and freshly distilled benzyl alcohol, warmed to 185° C. for ca. $\frac{3}{4}$ hour under a slow purge of nitrogen with provision for removal of methanol. The mixture is then heated with stirring at 180°–185° C. for an additional $\frac{1}{2}$ hour and cooled. The crude product is taken up in ethanol and this solution is added during $\frac{1}{4}$ hour to a mechanically stirred and filtered solution of ca. 0.5 molar proportion of curpic acetate monohydrate in water. The resulting somewhat oily suspension is stirred for ca. 4 hours, during which time the copper chelate of trans-2-carbobenzyloxy-3-carbomethoxycyclopentanone solidifies. The crude green solid is filtered, washed well with cold water and air dried. Recrystallization from ethanol affords an 80% yield of the pure copper chelate as lustrous green plates.

A solution of the pure crystalline copper chelate in chloroform is shaken in a separatory funnel with 25 percent (v/v) aqueous sulfuric acid until the organic phase is essentially colorless. The organic phase is separated and the aqueous phase is extracted with 25 ml of chloroform. The combined organic phases are washed several times with water, several times with 10 percent aqueous sodium bicarbonate solution and again with water and dried over anhydrous magnesium sulfate. The filtered solution is concentrated in vacuo to afford a 100 percent yield, based upon copper chelate, of the pure benzyl ester, obtained as a viscous, colorless oil.

STEP 3

In this step, position 2 is alkylated to introduce a required side chain. The side chain is introduced in its entirety in one step. Thereby, a wider range of side chains can be introduced than has heretofore been possible. The introduction of the desired side chain via a nucleophilic displacement utilizes any compound $NC(CH_2)_3C\equiv CCH_2X$ in which X is a good leaving group. Thus, to a mechanically stirred suspension of a mineral oil dispersion of sodium hydride in dry dimethoxyethane is added during 30 minutes a solution of a substantially equimolar proportion of trans-2-carbobenzyloxy-3carbomethoxy cyclopentanone in dry dimethoxyethane. Stirring is continued for ca. one hour after addition is complete, during which hydrogen evolution ceases. A solution of a substantially equimolar proportion of the methane sulfonate of 6-cyano-2-hexyne-1ol in dry dimethoxyethane is added during ca. 10 minutes while the mixture is gradually warmed to 65° C. Heating is discontinued for 15 minutes after addition is completed and the resulting light tan mixture is heated at reflux for ca. 5 hours, cooled, diluted with 150 ml of water and exhaustively extracted with ethyl acetate. The combined extracts are washed several times with NaCl brine and dried over anhydrous magnesium sulfate. The filtered solution is concentrated in vacuo to afford, (after washing by decantation several times with hexane and removal of residual solvent at the stripper) a 97% yield of crude product. Purification is accomplished via chromatography on silica gel, using benzene/methanol, (97/3), as solvent. The pure product, (80–85% yield, typically) is obtained as a viscous, faint yellow oil.

Other alkylating agents which can be used include compounds having the formula $NC(CH_2)_3C\equiv CCH_2X$ in which X is bromo, chloro, iodo or p-tolylsulfonyl; $Br(CH_2)_6CO_2CH_3$, $Br(CH_2)_6CN$ and $BrCH_2C\equiv CCH_2CH_3$. Broadly, the following alkylating agents are useful in the alkylation: cis-$XCH_2CH=CH(CH_2)_3CN$, $X(CH_2)_3(CH_2)_xCN$, $XCH_2C\equiv CH-CH_2Si(CH_3)_2CH_2CN$, $XCH_2C\equiv CCH_2SCH_2CN$, $XCH_2C\equiv C(CH_2)_3CO_2R$, $XCH_2C\equiv CCH_2N(CH_3)CH_2CN$, $XCH_2C\equiv CCH_2OCH_2CN$, $XCH_2C\equiv C(CH_2)_xCN$, $XCH_2C\equiv C(CH_2)_3SO_2NHCH_3$, cis-$XCH_2CH=CHCH_2SCH_2CN$, $XCH_2C\equiv CCH_2C(CH_3)_2CH_2CN$ and $XCH_2C\equiv CCH_2N(CH_2CN)_2$, wherein X is a good leaving group and x is 1 to 10 ($\neq$ 3).

The product of Step 3 is new.

In Step 4, the unwanted carbobenzyloxy group at the 2-position of the cyclopentanone moiety is removed readily by catalytic hydrogenolysis. The simultaneous reduction of the 2-hexynyl moiety of the side chain to the 2-hexenyl group using pyridine to prevent over reduction of the acetylenic group to an alkane group is believed to be patentable as is also the product, trans-2-(6'-cyano-cis -2'-hexenyl)-3-carbomethoxy cyclopentanone.

In Step 5, the carbomethoxy group in the 3-position on the cyclopentanone nucleus is saponified with aqueous methanolic sodium carbonate at about 75° C. to give, upon acidification with concentrated hydrochloric acid, the new Compound 6 having a carboxylic acid group in the 3-position. The reaction is a known type reaction.

In Step 6A, Compound 6 is transformed to its acid chloride by reaction with thionyl chloride in dry benzene under anhydrous conditions at about 85°–90° C. and, after recovery is employed immediately in the following step.

In Step 6B, the diol is prepared from the preceding acid chloride by reduction with alkali metal borohydride in p-dioxane in a conventional reduction at about 0° to 5° C. to give the new compound trans-2-(6-cyano-cis-2-hexenyl)-3-hydroxymethylcyclopentanol.

In Step 7, the 6-cyano-cis-2hexenyl group in position 2 is transformed to the corresponding 6-carbomethoxy -cis-2-hexenyl compound by hydrolyzing the cyano moiety to carboxylate with aqueous methanolic alkali metal hydroxide, liberating the acid from the resulting carboxylate salt with concentrated mineral acid, and treating the latter with diazomethane to give new product trans-2-(6'-carbomethoxy-cis-2'-hexenyl)-3-hydroxymethylcyclopentanol as a viscous oil.

In final Step 8, Compound 8 is selectively oxidized by adding a solution of it in a non-reactive solvent, advantageously methylene chloride, to a solution of anhydrous chromium trioxide in a mixture of about two molar proportions of anhydrous pyridine and one molar proportion of dry methylene chloride. The reaction is carried out at about 25° C. At the completion of the reaction, compound 9, trans-2-(6'-carbomethoxy- cis-2'-hexenyl)-3-formylcyclopentanone is recovered. As is well known to art-skilled persons, this compound is readily transformed to 11-deoxyprostaglandins via known steps.

The following examples describe completely representative specific embodiments of the invention and the best mode contemplated by the inventors of carrying out the invention.

EXAMPLE 1—Trans-2,3-dicarbomethoxycyclopentanone, 2

To a mechanically-stirred suspension of 30.5 g, 0.72 mole, of a 57 percent mineral oil dispersion of sodium hydride in 450 ml of dry p-xylene is added 20 ml of a solution of 142.5 g, 0.60 mole, of 1,2,4-tri-carbomethoxybutane in 125 ml of dry p-xylene and 1 ml of anhydrous methanol. After the reaction has commenced, the remainder of the ester solution is added at 20°–25° C. during 1.5 hours. Stirring is continued for 20 minutes after addition is complete, the viscous mixture is diluted with 200 ml of water and the phases are separated. The aqueous phase is immediately acidified by addition of a stirred solution of 45.0 g, 0.21 mole, of citric acid monohydrate in 125 ml of water. The crude product is extracted into three 250 ml portions of ethyl acetate and the combined organic phases are washed with 100 ml of water and with two 100 ml portions of sodium chloride brine and are dried over anhydrous magnesium sulfate. The filtered solution is treated with 7.0 g of decolorizing carbon, filtered again and concentrated in vacuo to afford 90.0 g, 75 percent, of crude product which crystallizes upon seeding. This material, which is 90–95 percent pure titular compound via VPC, should be recrystallized from ether/petroleum ether (30°–60° C.), and is then obtained as colorless needles, m.p. 49.0°–50.0° C.

Anal. Calc. for $C_9H_{12}O_5$: C, 53.99; H, 6.04. Found: C, 53.92; H, 6.01.

A 2,4-dinitrophenylhydrazone is obtained as golden felted needles, m.p. 145.0°–146.5° C., from methanol.

Anal. Calc. for $C_{15}H_{16}N_4O_8$: C, 47.37; H, 4.24; N, 14.73. Found: C, 47.41; H, 4.24; N, 14.71.

EXAMPLE 2—Trans-2-carbobenzyloxy-3-carbomethoxycyclopentanone, 3

A magnetically stirred mixture of 35.0 g, 0.175 mole, of 2,3-dicarbomethoxycyclopentanone and 25.1 g, 0.175 mole, of freshly distilled benzyl alcohol is warmed during 45 minutes to 185° C. under a slow purge of nitrogen with provision for removal of methanol. The mixture is then heated with stirring at 180°–185° C. for an additional 30 minutes and cooled. The crude product is taken up in 500 ml of ethanol and this solution is added during 15 minutes to a mechanically stirred and filtered solution of 18.0 g, 0.090 mole, of cupric acetate monohydrate in 1100 ml of water. The resulting somewhat oily suspension is stirred for 4 hours, during which time the copper chelate of the title compound solidifies. The crude green solid is filtered, washed well with cold water and air dried. Recrystallization from ethanol affords 44.8 g (80% yield) of pure copper chelate as lustrous green plates, m.p. 161.0°–163° C. (decomposition).

A solution of 36.0 g, 0.059 mole, of the pure crystalline copper chelate obtained above in 225 ml of chloroform is shaken in a separatory funnel with 90 ml of 25 percent (v/v) aqueous sulfuric acid until the organic phase is essentially colorless (3–5 minutes). The organic phase is separated and the aqueous phase is extracted with 25 ml of chloroform. The combined organic phases are washed with 3 × 100 ml of water, with 2 × 75 ml of 10 percent aqueous sodium bicarbonate solution and finally with 3 × 100 ml of water and are dried over anhydrous magnesium sulfate. The filtered solution is concentrated in vacuo to afford 34.0 g (100 percent yield, based upon copper chelate) of pure title commpound.

EXAMPLE 3—2-(6'-Cyano-2'-hexynyl)-2-carbobenzyloxy-3-carbomethoxycyclopentanone, 4

To a mechanically stirred suspension of 8.95 g, 0.214 mole, of a 57 percent mineral oil dispersion of sodium hydride in 200 ml of dry dimethoxyethane is added during 30 minutes a solution of 55.2 g, 0.200 mole, of trans-2-carbobenzyloxy-3-carbomethoxycyclopentanone in 50 ml of dry dimethoxyethane. Stirring is continued for one hour after addition is completed, during which hydrogen evolution ceases. A solution of 40.20 g, 0.200 mole, of the methane sulfonate of 6-cyano-2hexyne-1-ol in 20 ml of dry dimethoxyethane is added during 10 minutes while the mixture is gradually warmed to 65° C. Heating is discontinued for 15 minutes after addition is completed and then the light tan mixture is heated at reflux for 5 hours, cooled, diluted with 150 ml of water and exhaustively extracted with ethyl acetate. The combined extracts are washed with 3 × 80 ml of NaCl brine and are dried over anhydrous magnesium sulfate. The filtered solution is concentrated in vacuo to afford (after washing by decantation with 3 × 30 ml of hexane and removal of residual solvent at the stripper) 73.86 g (97% yield) of crude product. Purification is accomplished via chromatography on 800 g of silica gel, using benzene/methanol, (97/3), as solvent. The pure product (60–65 g, 80–85% yield, typically) is obtained as a viscous, faint yellow oil.

EXAMPLE 4—Trans-2-(6'-cyano-2'-hexenyl)-3-carbomethoxycyclopentanone, 5

A magnetically stirred mixture of 11.43 g, 0.030 mole, of 2-(6'-cyano-2'-hexynyl)-2-carbobenzyloxy-3-carbomethoxycyclopentanone, 4.75 g, 0.060 mole, of pyridine and 2.00 g of 5 percent palladium on barium sulfate in 125 ml of ethanol is hydrogenated at 25° C. and one atmosphere pressure. Hydrogen (1,347 ml, theoretical) is absorbed in 124 minutes and the reaction is terminated. The catalyst is filtered, washed with several small portions of ethyl acetate and the combined filrates are concentrated in vacuo. The residual oil is taken up in 125 ml of ethyl acetate, washed with three 25 ml portions of five percent aqueous hydrochloric acid, with 50 ml of water, with 50 ml of five percent aqueous sodium bicarbonate solution and finally with three 25 ml portions of NaCl brine and is dried over anhydrous magnesium sulfate. Filtration and concentration in vacuo affords 6.78 g (91.5 percent, crude yield) of product as a somewhat viscous, faintly yellow oil. Chromatography on 80 g of silica gel employing benzene/ethyl acetate (97/3) as solvent gives pure product as a colorless oil.

EXAMPLE
5—Trans-2-(6'-cyano-cis-2'-hexenyl)-3-carboxycyclopentanone, 6

A magnetically stirred mixture of 15.00 g, 0.061 mole, of crude trans-2-(6'-cyano-cis-2'-hexenyl)-3-carbomethoxycyclopentanone in 150 ml of 5 percent aqueous sodium carbonate solution and 25 ml of methanol is warmed in an oil bath at 75°–80° C. under a slight positive nitrogen pressure for 4 hours, cooled, and stirred at 25° C. overnight. The resulting solution is washed with three 25 ml portions of ethyl acetate and, while being chilled in an ice bath, is acidified with concentrated hydrochloric acid. The yellow oil which separates is extracted with three 50 ml portions of ethyl acetate and the combined extracts are washed with three 30 ml portions of NaCl brine and dried over anhydrous magnesium sulfate. Filtration and concentration in vacuo affords 12.6 g (89 percent) of crude acid as a viscous yellow oil. Purification is accomplished via slow chromatography on 160.0 g of silica gel, using chloroform as solvent. The pure product (10.6 g, 75 percent yield) is obtained as a colorless oil.

EXAMPLE
6—Trans-2-(6'-cyano-cis-2'-hexenyl)-3-hydroxymethylcyclopentanol, 7

A. Preparation of the acid chloride

A magnetically-stirred solution of 7.00 g, 0.030 mole, of trans-2-(6'-cyano-cis-2'-hexenyl)-3-carboxycyclopentanone and 6.85 g, 0.058 mole, of freshly distilled thionyl chloride in 175 ml of dry benzene is heated under anhydrous conditions in an oil bath at 85°–90° C. for 3 hours, cooled and concentrated in vacuo. An additional 25 ml of dry benzene is added and again the solution is concentrated in vacuo. After storing at 0.1 mm Hg for 2 hours, the quantitative yield of crude yellow-brown acid chloride is fully characterized by its IR and NMR spectra and is employed immediately in the next step.

B. Preparation of the diol, 7

To a chilled, magnetically-stirred suspension of 1.40 g, 0.037 mole, of sodium borohydride in 40 ml of p-dioxane and 40 ml of water is added during 30 minutes at 0°–5° C. a solution of all of the acid chloride obtained in A, above, in 40 ml of p-dioxane. After addition is complete, 0.40 g, 0.010 mole, of sodium borohydride is added cautiously and the foaming mixture is stirred at 0°–5° C. for one hour, after which 0.20 g, 0.005 mole, of sodium borohydride is added in one portion and stirring at 0°–5° C. is continued for 45 minutes. The cooling bath is then removed and the stirred mixture is warmed during 15 minutes to 25° C. and poured into 100 ml of sodium chloride brine. After exhaustive extraction with ethyl acetate, the combined extracts are washed with 75 ml of sodium chloride brine, with two 50 ml portions of 10 percent aqueous sodium bicarbonate solution and with two 50 ml portions of sodium chloride brine and the solution then is dried over anhydrous magnesium sulfate. The filtered solution is concentrated in vacuo to afford 6.0 g, 96 percent, of crude diol which is fully characterized by its IR and NMR spectra and is employed directly in the next steps.

EXAMPLE
7—Trans-2-(6'-carbomethoxy-cis-2'-hexenyl)-3-hydroxymethylcyclopentanol, 8

A magnetically-stirred suspension of 4.00 g, 0.018 mole, of trans-2-(6'-cyano-cis-2'-hexenyl)-3-hydroxymethylcyclopentanol in a solution of 7.00 g, 0.124 mole, of potassium hydroxide in 50 ml of water and 5 ml of methanol is heated at reflux for one hour, during which time the substrate dissolves. After cooling and washing with three 25 ml portions of ether, the yellow basic aqueous phase is treated with decolorizing carbon, chilled, neutralized with concentrated hydrochloric acid and extracted with three 25 ml portions of ethyl acetate. The combined extracts are washed with two 25 ml portions of sodium chloride brine, dried over anhydrous magnesium sulfate, filtered and concentrated in vacuo to afford 4.00 g, 93 percent, of crude acid product as a viscous, colorless oil.

A magnetically-stirred solution of 3.10 g, 0.013 mole, of the crude acid in 20 ml of ether and 5 ml of methanol is treated with a slight excess of ethereal diazomethane to a faint yellow color and stirred at 25° C. for one hour. The excess diazomethane is quenched by the dropwise addition of glacial acetic acid, and the resulting solution is diluted with 25 ml of ether, washed with two 15 ml portions of 5 percent aqueous sodium bicarbonate solution and with two 10 ml portions of sodium chloride brine and dried over anhydrous magnesium sulfate. The filtered solution is concentrated in vacuo to afford 3.15 g, 96 percent, of the carbomethoxy diol as a viscous colorless oil which, on the basis of its spectroscopic and silica gel TLC characterization, is employed directly in the final step.

EXAMPLE
8—Trans-2-(6'-carbomethoxy-cis-2'-hexenyl)-3-formylcyclopentanone, 9

To a mechanically-stirred, chilled solution of 9.840 g, 0.12440 mole, of anhydrous pyridine in 150 ml of dry methylene chloride is added in several portions during 15 seconds 6.320 g, 0.06220 mole, of anhydrous chromium trioxide. The cooling bath is removed and the resulting deep burgundy solution is stirred under dry nitrogen for 15 minutes. A solution of 1.328 g, 0.00518 mole, of trans-2-(6'-carbomethoxy-cis-2'-hexenyl)-3-hydroxymethylcyclopentanol in 3 ml of dry methylene chloride is added in one portion, washed in with an additional one ml of solvent and the resulting black tarry mixture is stirred at 25° C. for 20 minutes. The dark solution is decanted from the residue, which is washed with two 100 ml portions of methylene chloride and the combined organic phases are washed with three 100 ml portions of 5 percent aqueous sodium hydroxide, with 100 ml of 5 percent aqueous hydrochloric acid, with 100 ml of 5 percent aqueous sodium bicarbonate and finally with two 100 ml portions of sodium chloride brine. After being dried with anhydrous magnesium sulfate, the filtered solution is concentrated in vacuo to afford 1.240 g of crude product which is chromatographed on 20.0 g of silica gel using benzene/acetone, (98/2) as eluant. The titular keto-aldehyde 1.195 g, 92 percent, is obtained as a colorless, mobile oil which is pure by TLC and by IR, NMR and mass spectrometry and which may be employed directly in subsequent work in known ways to prepare 11-deoxyprostaglandins.

What is claimed is:

1. Trans-2-carbobenzyloxy-3-carbomethoxycyclopentanone.
2. 2-(6'-Cyano-2'-hexynyl)-2-carbobenzyloxy-3-carbomethoxycyclopentanone.
3. Trans-2-(6'-cyano-cis-2'-hexenyl)-3-carbomethoxycyclopentanone.
4. Trans-2-(6'-cyano-cis-2'-hexenyl)-3-chlorocarbonylcyclopentanone.
5. Trans-2-(6'-cyano-cis-2'-hexenyl)-3-hydroxymethylcyclopentanol.
6. Trans-2-(6'-carbomethoxy-cis-2'-hexenyl)-3-hydroxymethylcyclopentanol.